US008302195B2

(12) United States Patent
Kawamura (10) Patent No.: US 8,302,195 B2
(45) Date of Patent: Oct. 30, 2012

(54) SAMPLE ANALYZER, SAMPLE ANALYZING METHOD, AND COMPUTER PROGRAM PRODUCT

(75) Inventor: Yoshiyuki Kawamura, Kobe (JP)

(73) Assignee: Sysmex Corporation, Kobe (JP)

( * ) Notice: Subject to any disclaimer, the term of this patent is extended or adjusted under 35 U.S.C. 154(b) by 364 days.

(21) Appl. No.: 12/626,233

(22) Filed: Nov. 25, 2009

(65) Prior Publication Data

US 2010/0146625 A1 Jun. 10, 2010

(30) Foreign Application Priority Data

Dec. 5, 2008 (JP) ................................. 2008-310428

(51) Int. Cl.
*G06F 11/00* (2006.01)
*G06F 11/30* (2006.01)
(52) U.S. Cl. ............................ 726/24; 726/25; 713/188
(58) Field of Classification Search .................... 726/24, 726/25; 713/188
See application file for complete search history.

(56) References Cited

U.S. PATENT DOCUMENTS

| 2003/0084322 A1* | 5/2003 | Schertz et al. ................ 713/200 |
| 2003/0177397 A1* | 9/2003 | Samman ........................ 713/201 |
| 2004/0193895 A1 | 9/2004 | Kaneko |
| 2005/0228695 A1* | 10/2005 | Ito ..................................... 705/2 |
| 2007/0269897 A1 | 11/2007 | Tanaka et al. |
| 2008/0044912 A1 | 2/2008 | Yamamoto et al. |
| 2008/0097786 A1* | 4/2008 | Sachdeva .......................... 705/2 |
| 2008/0209513 A1* | 8/2008 | Graves et al. ..................... 726/2 |
| 2008/0311678 A1 | 12/2008 | Ootani et al. |
| 2009/0187348 A1 | 7/2009 | Ariyoshi |
| 2009/0241177 A1* | 9/2009 | Bluth ................................. 726/7 |

FOREIGN PATENT DOCUMENTS

JP 10-308737 A 11/1998

* cited by examiner

*Primary Examiner* — Mohammad W Reza
(74) *Attorney, Agent, or Firm* — Brinks Hofer Gilson & Lione (57) ABSTRACT

A sample analyzer comprising: a measuring unit for measuring a sample and outputting measurement data; and a measurement controller configured for carrying out operations comprising: obtaining analysis results of measurement data output from the measuring unit; detecting a malicious program; and restricting the output of the obtained analysis results when a malicious program has been detected, is disclosed. A sample analyzing method and a computer program product are also disclosed.

20 Claims, 10 Drawing Sheets

SAMPLE ANALYZER, SAMPLE ANALYZING METHOD, AND COMPUTER PROGRAM PRODUCT

RELATED APPLICATIONS

This application claims priority under 35 U.S.C. §119 to Japanese Patent Application No. JP2008-310428 filed on Dec. 5, 2008, the entire content of which is hereby incorporated by reference.

FIELD OF THE INVENTION

The present invention relates to a sample analyzer, sample analyzing method, and computer program product for analyzing samples such as blood, urine and the like.

BACKGROUND OF THE INVENTION

Various sample analyzers have been developed, such as apparatuses for measuring the size of cell particles in a sample such as urine, blood and the like, and analyzing the distribution of such particles.

Such sample analyzers are connected to an external computer via a network so as to be capable of data communication. Japanese Laid-Open Patent Publication No. 10-308737, for example, discloses an automatic analyzer capable of transmitting, to a specified terminal (personal computer), information relating to the analysis results and status of each analyzer using electronic mail.

However, the sample analyzer is at increased risk of infection by a computer virus due to the data communication via the network. Although reliability can not be guaranteed for the analysis results of a sample analyzer operating with software infected by a computer virus, conventional sample analyzers produce analysis results without distinguishing between the analysis results obtained prior to the infection and the analysis results obtained after the infection by a computer virus. There is concern, therefore, that despite the low reliability of the obtained analysis results, the operator of the sample analyzer may report the analysis results to the physician and patient without recognizing the fact of the low reliability of the obtained results.

SUMMARY OF THE INVENTION

The scope of the present invention is defined solely by the appended claims, and is not affected to any degree by the statements within this summary.

A first aspect of the present invention is a sample analyzer comprising: a measuring unit for measuring a sample and outputting measurement data; and a measurement controller configured for carrying out operations comprising: obtaining analysis results of measurement data output from the measuring unit; detecting a malicious program; and restricting the output of the obtained analysis results when a malicious program has been detected.

A second aspect of the present invention is a sample analyzer comprising: a measuring unit for measuring a sample and outputting measurement data; and a measurement controller configured for carrying out operations comprising: obtaining analysis results of measurement data output from the measuring unit; detecting a malicious program; and when a malicious program has been detected, stopping measuring a sample by the measuring unit, obtaining analysis results of the measurement data, or outputting the analysis result.

A third aspect of the present invention is a sample analyzing method comprising: measuring a sample and obtaining analysis results; detecting a malicious program; and restricting output of the obtained analysis results when a malicious program has been detected.

A fourth aspect of the present invention is a computer program product, comprising: a computer readable medium; and instructions, on the computer readable medium, adapted to enable a general purpose computer to perform operations, comprising: measuring a sample and obtaining analysis results; detecting a malicious program; and restricting the output of the obtained analysis results when a malicious program has been detected.

DETAILED DESCRIPTION OF THE PREFERRED EMBODIMENTS

The preferred embodiments of the present invention will be described hereinafter with reference to the drawings.

The present embodiment is described by way of example of a sample analyzer for blood or the like with a plurality of types of measuring units connected thereto, and is described concretely hereinafter based on the drawings.

Figure 1:
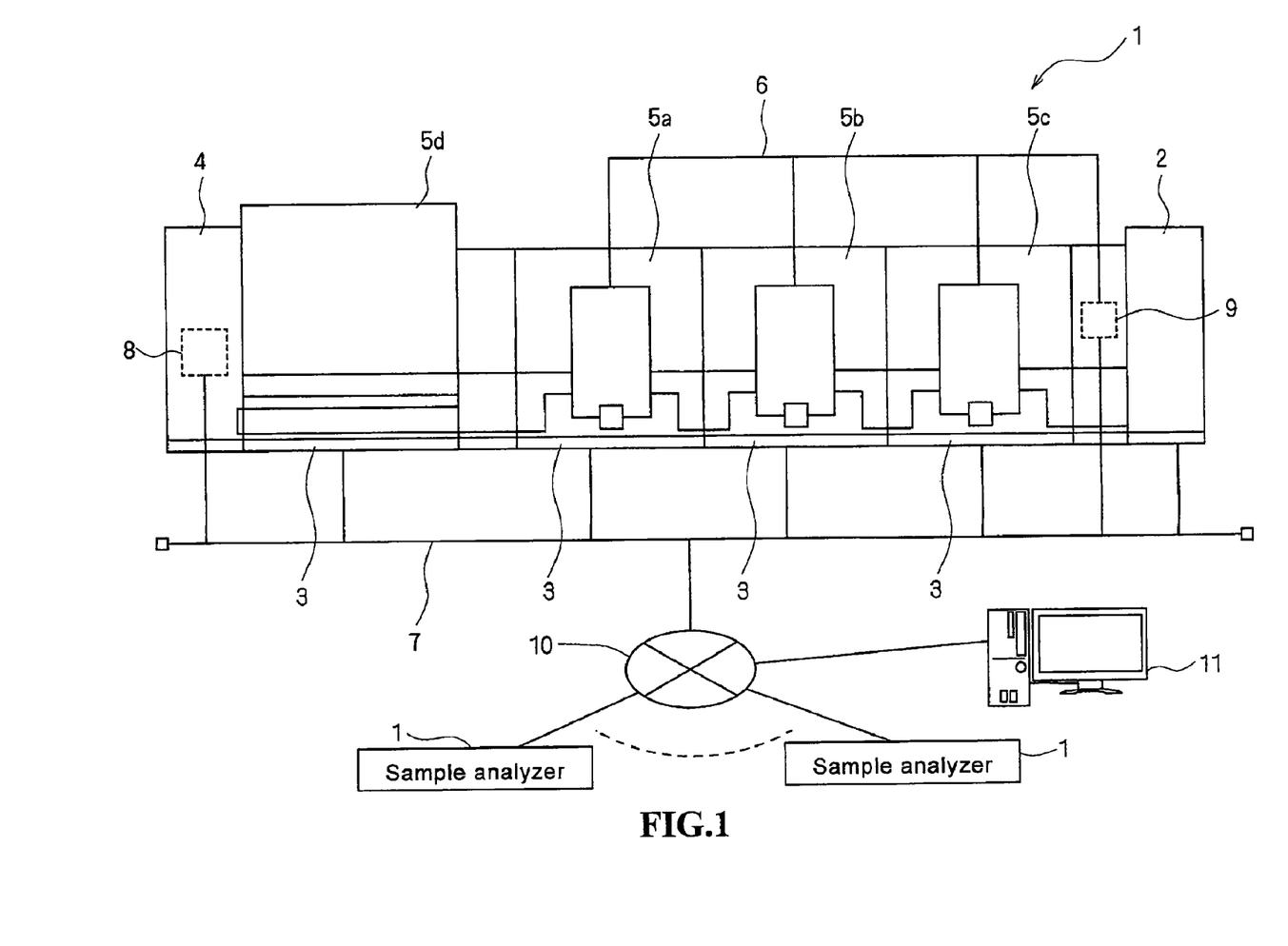
FIG. 1 is a schematic diagram briefly showing the structure of an embodiment of the sample analyzer of the present invention.

FIG. 1 is a schematic diagram briefly showing the structure of an embodiment of the sample analyzer of the present invention. The sample analyzer 1 of the embodiment of the present invention includes a sample acceptor device 2 for accepting a sample rack holding sample containers, A plurality of measuring units 5 (5a, 5b, 5c, 5d) for measuring samples, sample transporting devices 3 provided for each measuring unit 5 for transporting the sample racks, sample receiver 4 for receiving the sample rack after the sample has been extracted, transport control device 8, and control device 9.

The plurality of measuring units 5 may be the same type of measuring unit, or a plurality of types of measuring units 5a, 5b, 5c, 5d. Each set of a predetermined number of measuring units 5 are connected to a single control device 9 via a connecting cable 6. In the present embodiment, each set of three measuring units 5 are connected to a single control device 9 using a USB cable as the connecting cable 6.

The sample acceptor device 2 is configured so as to deliver a sample rack holding a plurality of sample containers to the sample transporting devices 3. The delivery of the sample rack is controlled by the transport control device 8, which is connected to the sample acceptor device 2 via a LAN 7 so as to be capable of data communication.

The transport control device 8 and the control device 9 are connected via a LAN 7 so as to be capable of data communication, and control the delivery of the sample rack in accordance with the connection status information relating to the connection status of the measuring units 5 obtained by the control device 9. The LAN 7 is also connected to an external network 10, and the network 10 is connected to an external server computer 11. The server computer 11 is connected to a plurality of other sample analyzers installed at different locations via the network 10 so as to be capable of data communication. The server computer 11 may be installed at the facility of the operator of the sample analyzers 1, and is capable of executing external accuracy management by totaling the analysis results of the accuracy management sample obtained by each sample analyzer 1, and executing remote maintenance by collecting the operation logs from each sample analyzer 1.

Figure 2:
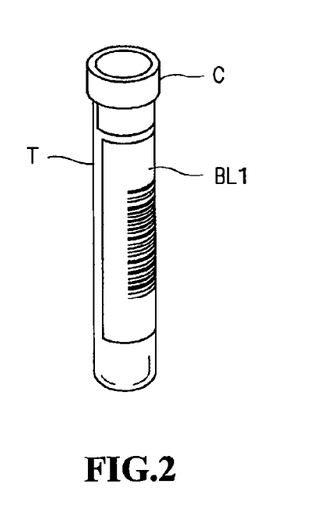
FIG. 2 is a perspective view of the exterior of a sample container.

FIG. 2 is a perspective view of the exterior of a sample container.

Figure 3:
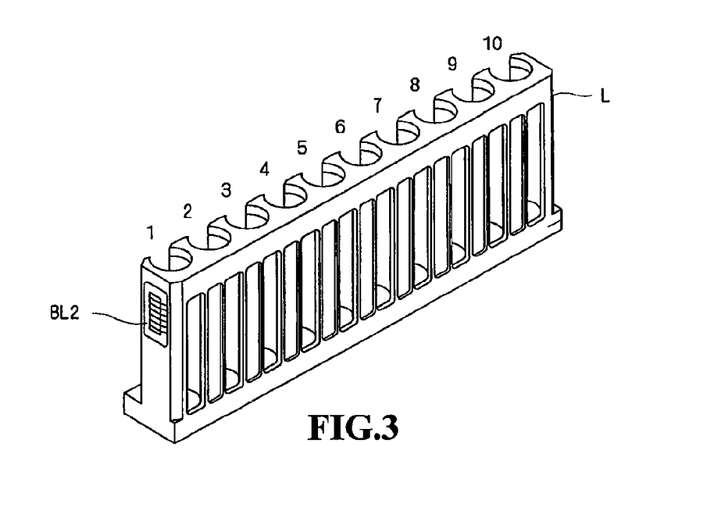
FIG. 3 is a perspective view showing the exterior of a sample rack.

FIG. 3 is a perspective view showing the exterior of a sample rack. As shown in FIG. 2, the sample container T is tube-like, and has an open top end.

The interior of the sample container T can accommodate, for example, a blood sample collected from a patient, and the opening at the top end can be sealed by a stopper C. A barcode label BL1 bearing a printed barcode identifying the sample is adhered to the side surface of the sample container T. As shown in FIG. 3, the sample rack L is configured to hold ten sample containers T in a vertical state (upright state). A barcode label BL2 bearing a printed barcode identifying the sample rack L is adhered to the side surface of the sample rack L.

The sample analyzer 1 shown in the example of FIG. 1 has four sample transporting devices 3 arranged at the front (toward the bottom of the drawing in FIG. 1) of the four measuring units 5a, 5b, 5c, 5d. The sample rack L is delivered between the adjacent sample transporting devices 3. The sample transporting device 3 disposed farthest to the right side in FIG. 1 starts the transport of the sample rack L delivered from the sample acceptor device 2. The sample transporting device 3 disposed farthest to the left side in FIG. 1 conveys the sample rack L to the sample receiving device 4.

Figure 4:
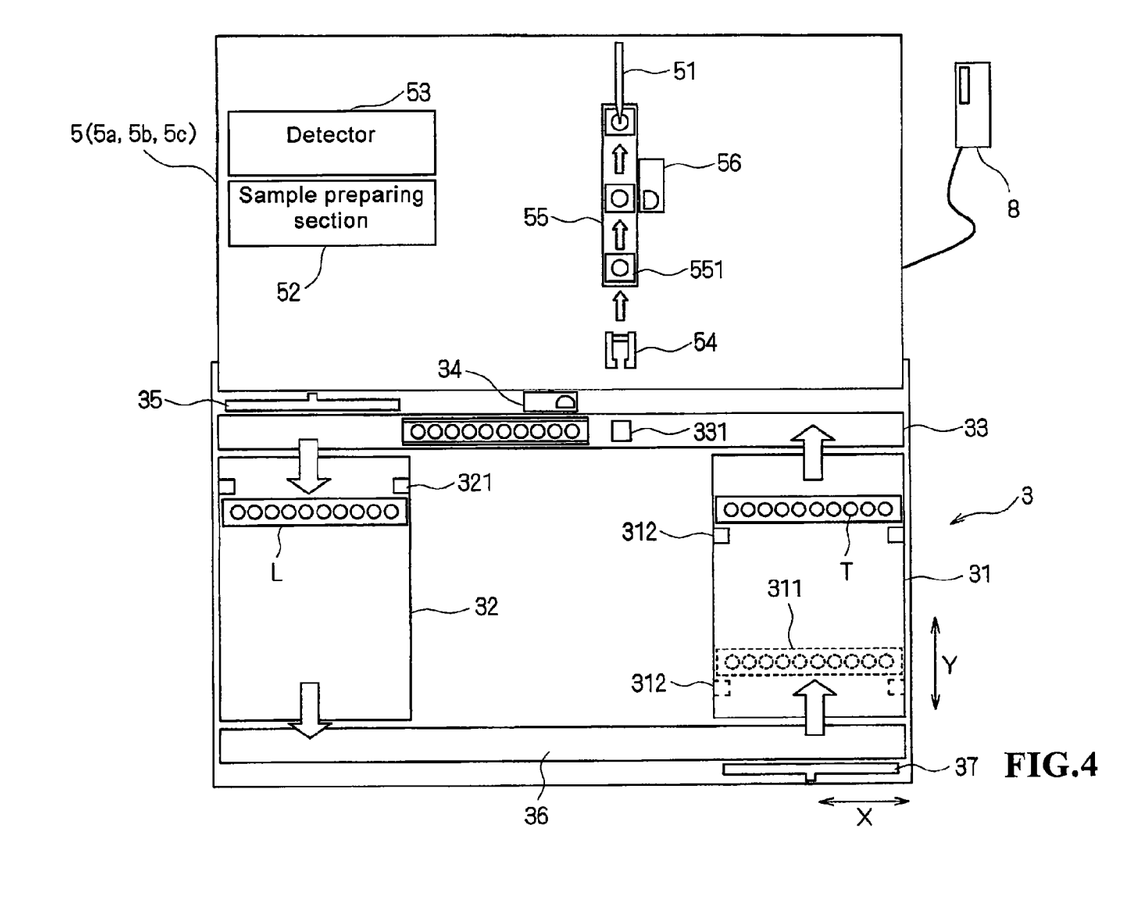
FIG. 4 is a schematic diagram briefly showing the structure of the measuring unit and the sample conveyor.

FIG. 4 is a schematic view briefly showing the structure of the measuring unit 5 and the sample transporting device 3. As shown in FIG. 4, the sample transporting device 3 includes a pre-analysis rack retainer 31 for temporarily retaining a plurality of sample racks L which hold sample containers T filled with unmeasured sample, post-analysis rack retainer 32, rack conveyor 33 for linearly moving the sample rack L in the arrow X direction, barcode reader 34 for reading the barcodes, rack mover 35 for moving the sample rack L to the post-analysis rack retainer 32, rack mover 36 for moving the sample rack L in the arrow X direction, and rack mover 37 for moving the sample rack L to the pre-analysis rack retainer 31.

The sample rack L is delivered to the pre-analysis rack retainer 31 by moving the rack mover 37 in the arrow Y direction. When the sample rack L is delivered to the rack detection position 311, the sample rack L is engaged by a rack feeder 312 which protrudes from the bottom side of the pre-analysis rack retainer 31 toward the inner side. The rack feeder 312 moves together with the engaged sample rack L in a direction approaching the rack mover 33 in conjunction with the movement in the direction approaching the rack conveyor 33. Note that the position of the sample rack L may be detected by a sensor (not shown in the drawing).

The rack conveyor 33 moves the sample rack L, which has been delivered by the pre-analysis rack retainer 31, in the X direction (from right to left in FIG. 4). When the sample container T delivered to the sample supplying position 331, the sample within is supplied to the measuring unit 5 by the holder of the measuring unit 5 gripping the sample container T and removing the sample container T from the sample rack L and aspirating the sample, whereupon the sample container T is returned to the sample rack L.

The rack mover 35 is positioned so as to face the post-analysis rack retainer 32 with the rack mover 33 disposed therebetween, and moves linearly in the arrow Y direction. The sample rack L is moved from the rack conveyor 33 to the post-analysis rack retainer 32 via the movement of the rack mover 35. When the sample rack L has been delivered, the sample rack L is engaged by a rack feeder 321 protruding from the bilateral bottom sides toward the inner side of the post-analysis rack retainer 32. The rack feeder 321 moves together with the engaged sample rack L in a direction approaching the rack mover 36 in conjunction with the movement of the rack feeder 321 toward the rack mover 36.

The sample receiving device 4 is capable of receiving a plurality of sample racks L. A sample rack L holding sample container T, from which the sample has been aspirated by the measuring unit 5, is transported by the sample transporting device 3 and received by the sample receiving device 4.

The conveyance of the sample rack L by the sample transporting device 3 is controlled by a transport control device 8, which is connected to the sample transport device 3 via a LAN so as to be capable of data communication. That is, the transport control device 8 controls the conveyance of the sample rack L by the sample transport device 3 from the reception of the rack L by the sample acceptor device 2, and the reception of the sample rack L from the sample transport device 3 to the sample receiver 4.

Note that the sample acceptor device 2, sample transport device 3, and sample receiver 4 may also be respectively provided with a controller, which is connected to the transport control device 8 and control device 9 so as to be capable of data communication. In this case, the transport control device 8 determines which measuring unit 5 is the destination and the route to the destination measuring unit 5 for the sample rack L and executes controls for instructing the various controllers to achieve same, and the controllers control the conveyance of the sample rack L according to the determines route.

Figure 5:
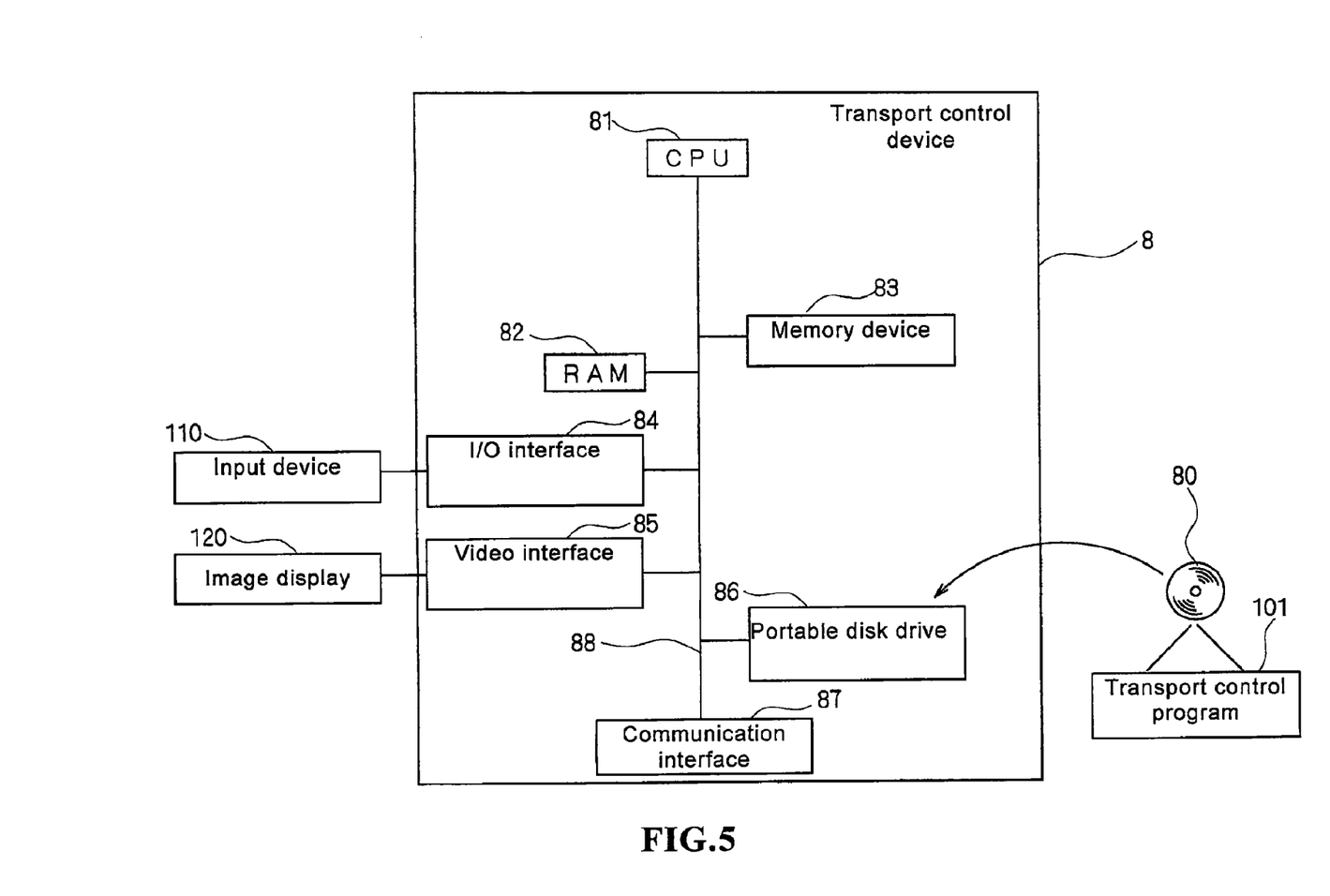
FIG. 5 is a block diagram showing the structure of the transport control device of the embodiment of the present invention.

FIG. 5 is a block diagram showing the structure of the transport control device 8 of the embodiment of the present invention. As shown in FIG. 5, the transport control device 8 is configured by a CPU 81, RAM 82, storage device 83, input/output (I/O) interface 84, video interface 85, portable disk drive 86, communication interface 87, and an internal bus 88 connected to these hardware components.

The CPU 81 is connected to each hardware component of the transport control device 8 via the internal bus 88, and executes controls of the operation of each hardware component, and performs various software functions according to a transport control program 101 stored in the storage device 83. The RAM 82 is configured by a volatile memory such as an SRAM, SDRAM or the like, and is used for the expanding the modules loaded during the execution of the transport control program 101, and storing the temporary data generated during the execution of the transport control program 101.

The storage device 83 is configured by a ROM or internal fixed storage device (hard disk) or the like. The transport control program 101 stored in the storage device 83 downloaded by the portable disk drive 86 from a portable recording medium such as a DVD or CD-ROM for recording information such as programs and data, and expanded during execution from the storage device 83 to the RAM 82. Of course, the transport control program 101 may also be a computer program downloaded from an external computer connected to the network via the communication interface 87.

The communication interface 87 is connected to the internal bus 88, and is capable of transmitting and receiving data to/from external computers when connected to an external network such as the Internet, a WAN, or LAN. In the present embodiment, the control device 9 and sample transport devices 3 and the like are connected via the LAN 7. Data can also be transmitted and received to/from the server computer 11 via the network 10.

The I/O interface 84 is connected to an input device 110 such as a keyboard and mouse for receiving data input. The video interface 85 is connected to an image display device 120 such as an LCD for displaying predetermined images.

The server computer 11 is, similar to the transport control device 8, configured by a CPU, RAM, storage device, I/O interface, video interface, portable disk drive, communication interface, and an internal bus connected to these various hardware components.

The plurality of measuring units 5 may be structurally the same type or structurally different types. In the example of FIG. 1, two measuring units 5a and 5c are the same type, whereas the remaining two measuring devices 5b and 5d are different types of measuring units. Specifically, the measuring units 5a and 5c are blood cell analyzers; for example, the measuring unit 5a counts the number of blood cells via an electrical resistance method, whereas the measuring unit 5c counts the number of blood cells by an optical method, then each measuring unit prepares a scattergram which is color coded for each type of blood cell, and displays the scattergram. The measuring unit 5b is a hemoglobin concentration measuring device for measuring the concentration of hemoglobin A1c (HgbA1c) in a blood sample, and the measuring unit 5d is a smear sample preparing device for preparing smear samples.

FIG. 4 briefly shows the configuration when the measuring units 5 are blood cell analyzers or hemoglobin concentration measuring devices (measuring units 5a, 5b, 5c, 5d). The measuring units 5 have a sample aspirator 51 for aspirating a blood sample form the sample container T, sample container conveyor 55 for transporting the sample container T to the aspirating position, barcode reader 56, sample preparing unit 52 for preparing a measurement sample from the aspirated blood to be used in measurements, and detector 53 for detecting the blood cells from the prepared measurement sample.

The sample container conveyor 55 is provided with a holder 54 for gripping the sample container T, and a sample container setting unit which has holes for inserting the sample container T. When the sample container T is positioned at the sample supplying position 331 and still held in the sample rack L, the sample container holder 54 of the sample container conveyor 55 grips the sample container T and moves in the arrow Y direction to insert the sample container T in the hole of the sample container setting unit 551. The sample container setting unit 551 is then moved and the barcode reader 56 reads the barcode, and the sample is aspirated from the sample container T by the sample aspirator 51.

In the sample preparing unit 52, a sample is prepared by adding a supplied reagent to the sample previously aspirated from the sample container T. In the detector 53, for example, in the case of WBC detection, the prepared sample is irradiated by laser light and the white blood cells in the sample are detected by flow cytometry. The detection results are transmitted to the control device 9 as electrical signals. US Patent Application No. 2009-187248 is hereby incorporated by reference in its entirety as though fully and completely set forth herein.

Figure 6:
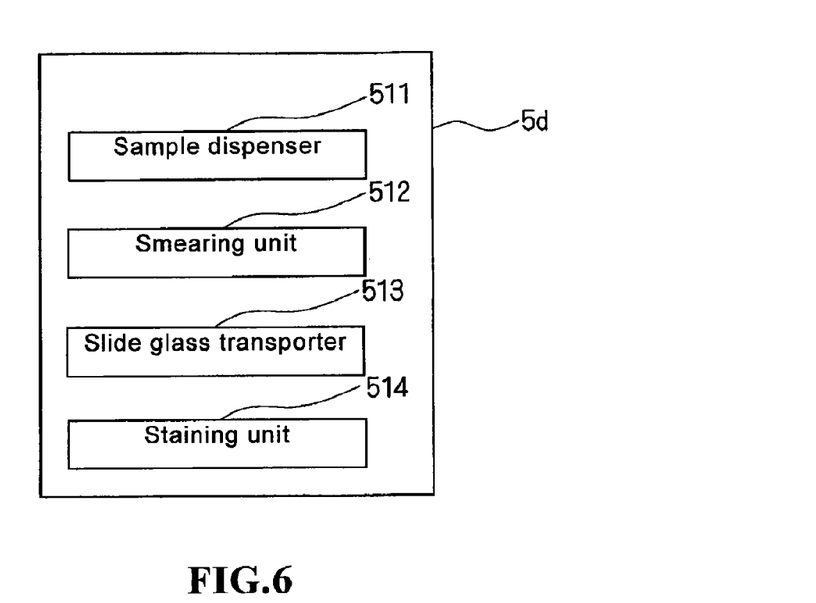
FIG. 6 is a block diagram showing a structural example when the measuring unit is a smear sample preparing device.

FIG. 6 is a block diagram showing a structural example when the measuring unit 5 is a smear sample preparing device. As shown in FIG. 6, the measuring unit 5d being used as a smear sample preparing device is provided with a sample dispenser 511, smearing unit 512, slide glass transporter 513, and staining unit 514.

The sample dispenser 511 is configured similar to the sample aspirator 51, sample container conveyor 55 and the like shown in FIG. 4; the sample dispenser 511 drips a blood sample aspirated from the sample container T by an aspirating tube (not shown in the drawing) equivalent to the sample aspirator 51 onto a slide glass. The smearing unit 512 smears and dries the blood sample dripped onto the slide glass, and prints identification information on the slide glass.

The slide glass transporter 513 accommodates the slide glass on which the blood sample is smeared in a transport cassette. The staining unit 514 supplies staining solution to the slide glass which has been transported to the staining position in the cassette. The smear sample prepared by smearing and staining is subjected to processing in the blood cell image display device (not shown in the drawing). Accordingly, the sample detection is not performed by the measuring unit 5d which prepares the smear sample. Note that the type of measuring unit 5 is not limited inasmuch as the measuring unit 5 may also be a urine analyzer, blood coagulation measuring apparatus, immunoanalyzer, gene amplification measuring apparatus and the like. US Patent Application No. 2007-269897, US Patent Application No. 2008-44912, and US Patent Application No. 2008-311678 are hereby incorporated by reference in its entirety as though fully and completely set forth herein.

Figure 7:
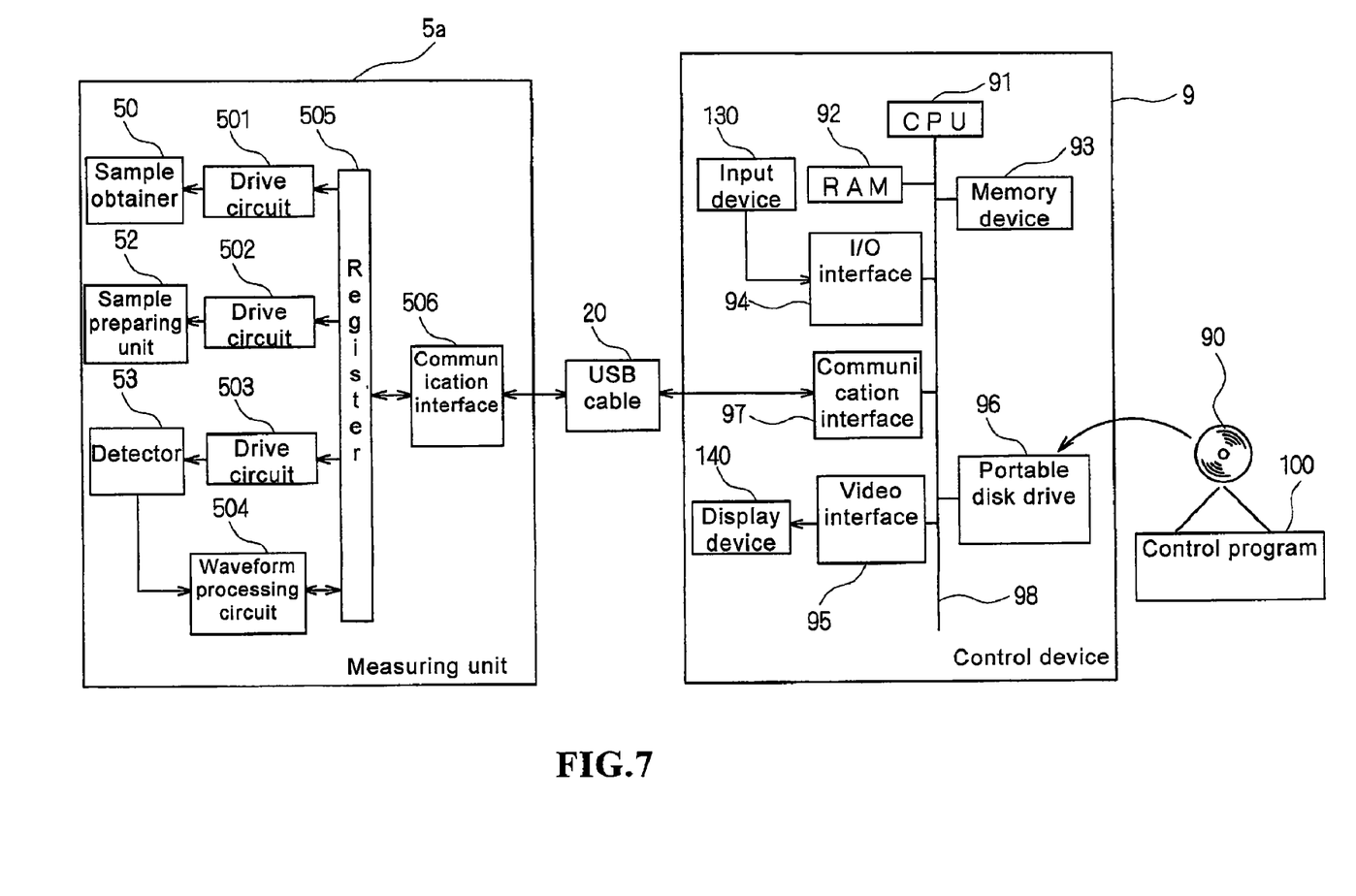
FIG. 7 is a block diagram showing the structure of the measuring unit and the control device of the embodiment of the sample analyzer of the present invention.

FIG. 7 is a block diagram showing the structure of the measuring unit 5 and the control device 9 of the sample analyzer 1 of the embodiment of the present invention. The example of FIG. 7 shows the structure of the measuring unit 5a, a blood cell analyzer. As shown in FIG. 7, the measuring unit 5 (5a) is provided with a sample obtainer 50, drive circuit 501 for driving the sample obtainer 50, sample preparing unit 52, drive circuit 502 for driving the sample preparing unit 52, detector 53, drive circuit 503 for driving the detector 53, and waveform processing circuit 504 for performing waveform processing of the electrical signals output from the detector 53.

The sample obtainer 50 and the sample preparing unit 52 are driven by control signals corresponding to control data stored in a register 505 and output by the drive circuit 501 and drive circuit 502. The detector 53 converts, for example, the obtained optical signals to electrical signals, the waveform processing circuit 504 amplifies the converted and transmitted electrical signals, the subjects the amplified electrical signals to waveform processing. The register 505 stores the waveform processed electrical signals.

The communication interface 506 is a USB serial interface connected to the communication interface 97 of the control device 9 via a USB cable 20. In this way the control device 9 can obtain information relating to the connected measuring unit 5 (5*a*) when connected via the USB cable 20.

The control device 9 is configured by CPU 91, RAM 92, storage device 93, I/O interface 94, video interface 95, portable disk drive 96, communication interface 97, and internal bus 98 which is connected to the various hardware components.

The CPU 91 is connected to each hardware component of the control device 9 via the internal bus 98, and executes controls of the operation of each hardware component, and performs various software functions according to a computer program 100 stored in the storage device 93. The RAM 92 is configured by a volatile memory such as an SRAM, SDRAM or the like, and is used for the expanding the modules loaded during the execution of the computer program 100, and storing the temporary data generated during the execution of the computer program 100.

The storage device 93 is configured by a ROM or internal fixed storage device (hard disk) or the like. The computer program 100 stored in the storage device 93 downloaded by the portable disk drive 96 from a portable recording medium such as a DVD or CD-ROM for recording information such as programs and data, and expanded during execution from the storage device 93 to the RAM 92. Of course, the computer program 100 may also be a computer program downloaded from an external computer connected to the network via the communication interface 97.

The communication interface 97 is connected to the internal bus 98, and is capable of transmitting and receiving data to/from external computers when connected to an external network such as the Internet, a WAN, or LAN. In the present embodiment, the transport control device 8 and sample transport devices 3 are connected via the LAN 7. Data can also be transmitted and received to/from the server computer 11 via the network 10.

The I/O interface 94 is connected to an input device 130 such as a keyboard and mouse, and receives data input. The video interface 95 is connected to an image display device 140 such as an LCD, CRT monitor or the like for displaying predetermined images.

In the sample analyzer 1 of the present embodiment, the control device 9 obtains the analysis results of the measurement data measured by the plurality of measuring units 5, selects a predetermined measurement result, and transmits the selected measurement result to the server computer 11 via the network 10. When the server computer 11 or other external computer is infected with a virus due to the data communication enabled connection via the network 10, there is a high probability that the computer virus may infect computer operating the control device 9, transport control device 8, measuring units 5 by the data sent via data communication.

In the present embodiment, the control device 9 and the transport control device 8 determine whether a malicious program is present, and when it has been determined that a malicious program is present, it is determined that the output analysis result has low reliability and various processes are executed. Whether a malicious program is present may be determined using a commercial virus detection program or by determining whether a program is present which is not on a computer program list introduced at initialization.

Figure 8:
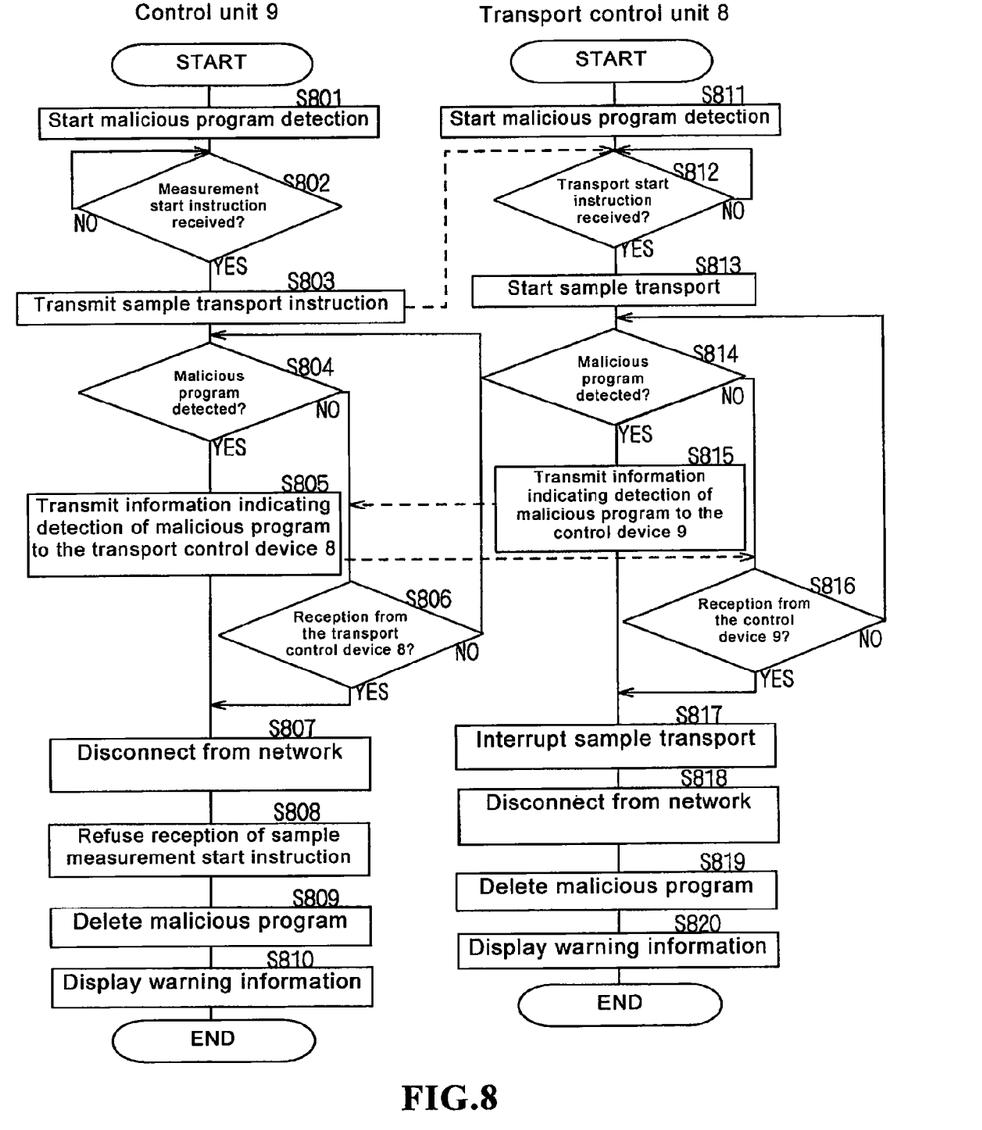
FIG. 8 is a flow chart showing the sequence of the analysis result output process performed by the CPU of the transport control device and the CPU of the sample analyzer control device of the embodiment of the present invention.

FIG. 8 is a flow chart showing the sequence of the analysis result output process performed by the CPU 81 of the transport control device 8 and the CPU 91 of the control device 9 of the sample analyzer 1 of the present embodiment. In FIG. 8, the CPU 91 of the control device 9 of the sample analyzer 1 of the present embodiment starts the malicious program detection process (step S801). Thereafter, the malicious program detection is continuously executed at predetermined intervals (for example, every 30 seconds). Specifically, the program list introduced beforehand is stored ahead of time on the storage device 93, and each program is queried at startup to determine whether a program name is present that is not on the list stored on the storage device 93. Of course, a commercial virus detection program may also be started.

A program such as, for example, VirusBuster (Trend Micro Corporation) may be used as the commercial virus detection program. In this case, the load on the CPU can be reduced and adverse effects on other running computer programs can be avoided if the function of detecting (real time search) a malicious program infecting the control device 9 via the network is enabled and the function of detecting (virus search) a malicious program already present on the control device 9 is disabled. When it is desirable to detect a malicious program that may already be present on the control device 9, the virus detection program may be set to start automatically (virus search) at shutdown of the control device 9. During sample measurements, the load on the CPU can be reduced and more reliable malicious program detection can be executed by setting the virus detection program so as to only determine whether newly generated files harbor a malicious program.

The CPU 91 determines whether a sample measurement start instruction has been received (step S802); the CPU 91 enters the standby state when the CPU 91 determines that a sample measurement start instruction has not been received (step S802: NO). When the CPU 91 determines that a sample measurement start instruction has been received (step S8902: YES), the CPU 91 transmits a sample transport instruction to the transport control device 8 (step S803). Specifically, a transport instruction is transmitted by pressing a start button or the like on the control device 9.

The CPU 81 of the transport control device 8 starts the malicious program detection (step S811). Thereafter, the malicious program detection is continuously executed at predetermined intervals (for example, every 30 seconds). Specifically, the program list introduced beforehand is stored ahead of time on the storage device 83, and each program is queried at startup to determine whether a program name is present that is not on the list stored on the storage device 83. Of course, a commercial virus detection program may also be similarly started as described above.

The CPU 81 then determines whether a sample transport instruction has been received (step S812); The CPU 81 enters the standby state when the CPU 81 determines that a sample transport instruction has not been received (step S812: NO). When the CPU 81 determines that a transport instruction has been received (step S812: YES), the CPU 81 starts the transport of the sample in accordance with the transport control program 101 stored in the storage device 83 (step S813).

The CPU 91 of the control device 9 determines whether the presence of a malicious program has been detected (step S804); when the CPU 91 determines that the presence of a malicious program has been detected (step S804: YES), the CPU 91 transmits information indicating a malicious program has been detected to the transport control device 8 (step S805). When the CPU 91 determines that the presence of a malicious program has not been detected (step S804: NO), the CPU 91 then determines whether information indicating a malicious program has been detected has been received from the transport control device 8 (step S806). When the CPU 91 determines that information indicating that the presence of a malicious program has been detected has not been received from the transport control device 8 (step S806: NO), the CPU 91 returns to the process of step S804 and the above described steps are repeated.

The CPU 81 of the transport control device 8 determines whether the presence of a malicious program has been detected (step S8144); when the CPU 81 determines that the presence of a malicious program has been detected (step S814: YES), the CPU 81 transmits information indicating that a malicious program has been detected to the control device 9 (step S815). When the CPU 81 determines that the presence of a malicious program has not been detected (step S814: NO), the CPU 81 then determines whether information indicating a malicious program has been detected has been received from the control device 9 (step S816). When the CPU 81 determines that information indicating that the presence of a malicious program has been detected has not been received from the control device 9 (step S816: NO), the CPU 81 returns to the process of step S814 and the above described steps are repeated.

When the CPU 91 of the control device 9 determines that information indicating a malicious program has been detected has been received from the transport control device 8 (step S806: YES), the CPU 91 then disconnects from the network 10 (step S807), and refuses to receive a sample measurement start instruction (step S808). The CPU 91 deletes the detected malicious program (step S809), and displays warning information on the display 140 (step S810).

When the CPU 91 of the control device 9 determines that the presence of a malicious program has been detected (step S804: YES), the processes of steps S807 through S810 are executed even when step S805 has been executed.

When the CPU 81 of the transport control device 8 determines that information indicating a malicious program has been detected has been received from the control device 9 (step S816: YES), the CPU 81 interrupts the transport of the sample (step S817), and disconnects from the network 10 (step S818). The CPU 81 deletes the detected malicious program (step S819), and displays warning information on the display 120 (step S820).

The CPU 81 of the transport control device 8 then also determines that the presence of a malicious program has been detected (step S814: YES), and executes the processes of steps S817 through 820 even when step S815 has been executed.

Figure 9:
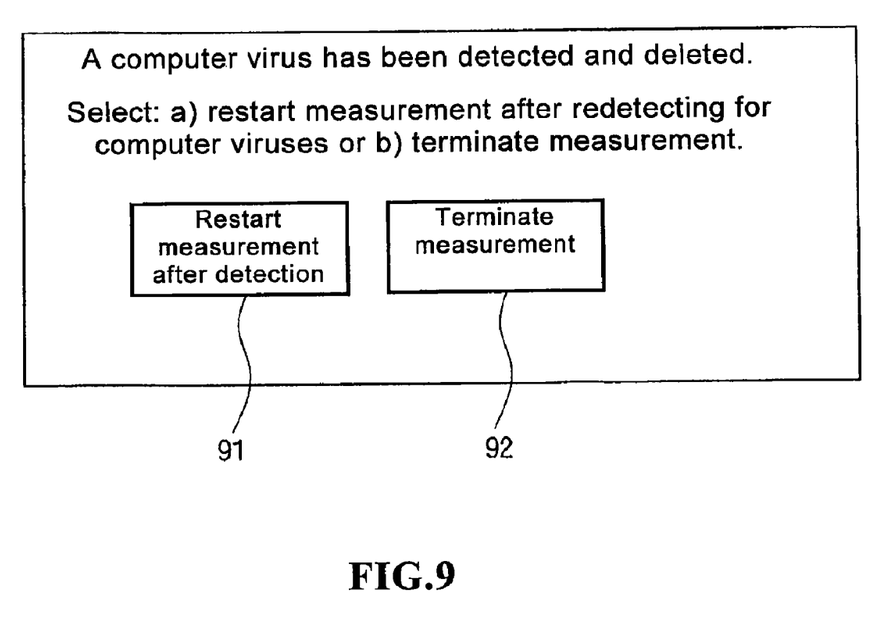
FIG. 9 shows an example of a warning information display screen which is displayed on the image display of the transport control device and the display unit of the control device.

FIG. 9 shows an example of a warning information display screen displayed on the image display 120 of the transport control device 8 or the display 140 of the control device 9. As shown in FIG. 9, when the malicious program is a computer virus, a message indicating that a computer virus has been detected and a message prompting for post-infection instruction input are displayed. The measurement process is suspended when a [measurement stop] button 92 is clicked with a mouse or the like. The measurement process is restarted after the measurement environment has been put in order when a [post-search measurement restart] button 91 is clicked by a mouse or the like.

Figure 10:
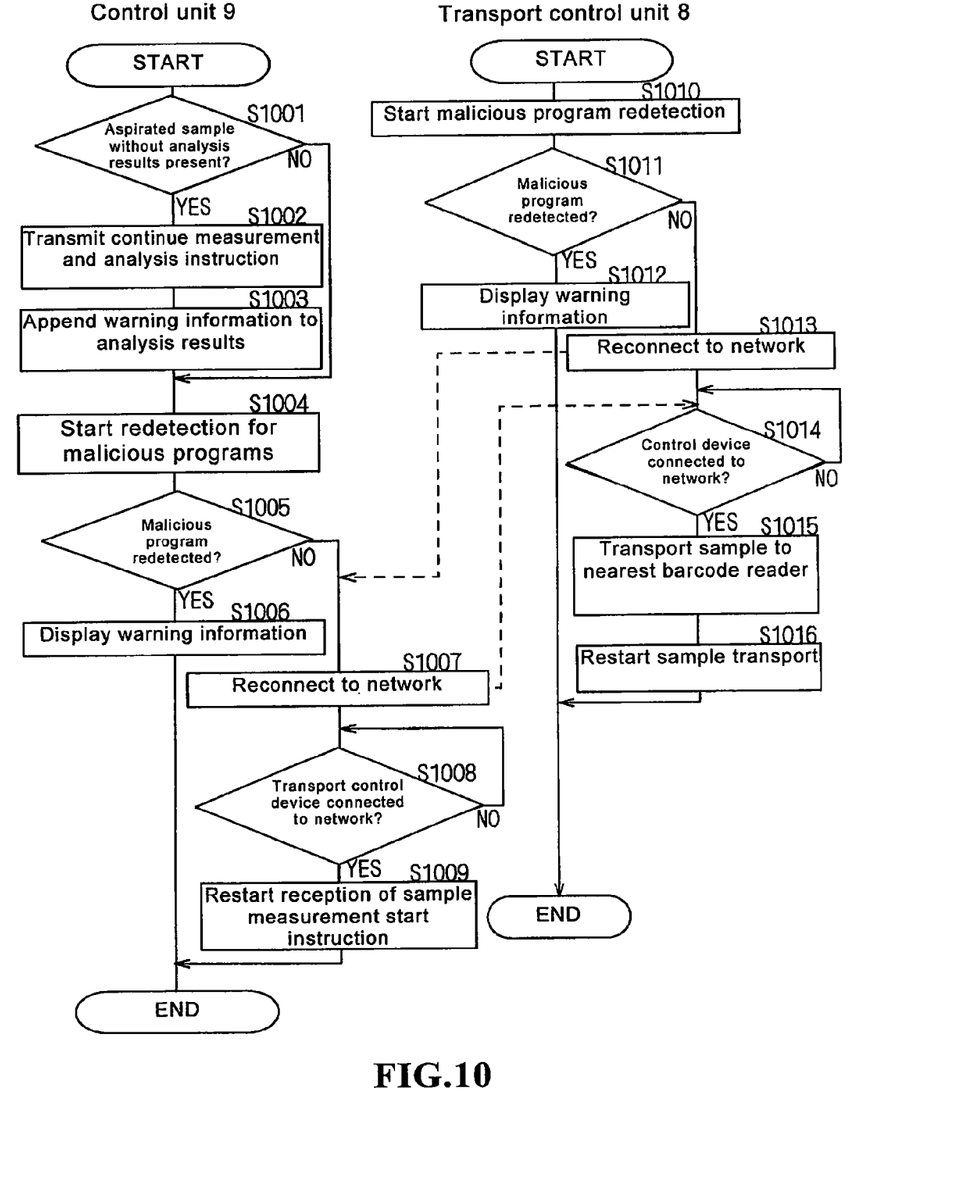
FIG. 10 is a flow chart showing the sequence of the measurement restart process performed by the CPU of the transport control device and the CPU of the sample analyzer control device of the embodiment of the present invention.

FIG. 10 is a flow chart showing the sequence of the measurement restart process performed by the CPU 81 of the transport control device 8 and the CPU 91 of the control device 9 of the sample analyzer 1 of the embodiment of the present invention. This process is started and executed when a malicious program is detected in the analysis result output process shown in FIG. 8. In FIG. 10, the CPU 91 of the control device 9 of the sample analyzer 1 of the embodiment of the present invention, for example, determines whether there is a sample present which has been aspirated by the sample aspirator 51 of the measurement unit 5 shown in FIG. 4 but for which the analysis result has not been output (step S1001). Since the determination process can be executed over the connection cable 6, that is, the USB cable, this process can be executed even when the connection to the network 10 over the LAN 7 has been disconnected.

When the CPU 91 determines there is a sample present which has been aspirated but for which the analysis result has not been output (step S1001: YES), the CPU 91 transmits instructions to continue the measurement and analysis of that sample to the measuring units 5 (step S1002), and appends warning information to the analysis result (step S1003). When the CPU 91 determines that is no sample which has been aspirated but for which analysis results have not been output (step S1001: NO), the CPU 91 skips steps S1002 and S1003, and restarts the malicious program detection (step S1004). Note that the CPU 91 may also stop the outputting of the analysis result when the CPU 91 determines that an aspirated sample is present for which the analysis result has not been output (step S1001: YES). The measurement process performed by the measuring units 5 may be stopped to prevent obtaining of the analysis result, or the analysis process of the measurement data output from the detector 53 may be stopped to prevent the obtaining of the analysis result.

The CPU 91 determines whether the malicious program has been redetected (step S1005); when the CPU 91 determines the presence of a malicious program has been detected (step S1005: YES), the CPU 91 determines that a malicious program has been redetected and deletes the malicious program, then displays warning information on the display 140 (step S1006).

The CPU 81 of the transport control device 8 then restarts the malicious program detection (step S1010). The CPU 81 determines whether the presence of a malicious program has been detected (step S1011); when the CPU 81 determines the presence of a malicious program has been detected (step S1011: YES), the CPU 81 determines that a malicious program has been redetected and deletes the malicious program, then displays warning information on the display 120 (step S1012). When the CPU 81 determines that the presence of a malicious program has not been detected (step S1011: NO), the CPU 81 reconnects to the network 10 (step S1013).

When the CPU 91 of the control device 9 determines that the presence of a malicious program has not been detected (step S1005: NO), the CPU 91 reconnects to the network 10 (step S1007), and determines whether the transport control device 8 has reconnected to the network (step 1008). The CPU 91 enters the standby state when the CPU 91 determines that the transport control device 8 has not reconnected to the network (step S1008: NO).

When the CPU 91 determines that the transport control device 8 has reconnected to the network 10 (step S1008: YES), the CPU 91 restarts reception of instructions to start measurements of samples (step S1009), and the process ends.

The CPU 81 of the transport control device 8 determines whether the control device 9 has reconnected to the network 10 (step S1014). The CPU 81 enters the standby state when the CPU 81 determines that the control device 9 has not reconnected to the network 10 (step S1014: NO).

When the CPU 81 determines that the control device 9 is connected to the network 10 (step S1014: YES), the CPU 81 transports the sample to the nearest barcode reader 34 (step S1015). The CPU 81 can verify the current transport position of each sample by reading the sample ID via the barcode reader 34, thus preventing transport error due to position error. After the CPU 81 completes the sample position verification, sample transport is restarted (step S1016), and the process ends.

Figure 11:
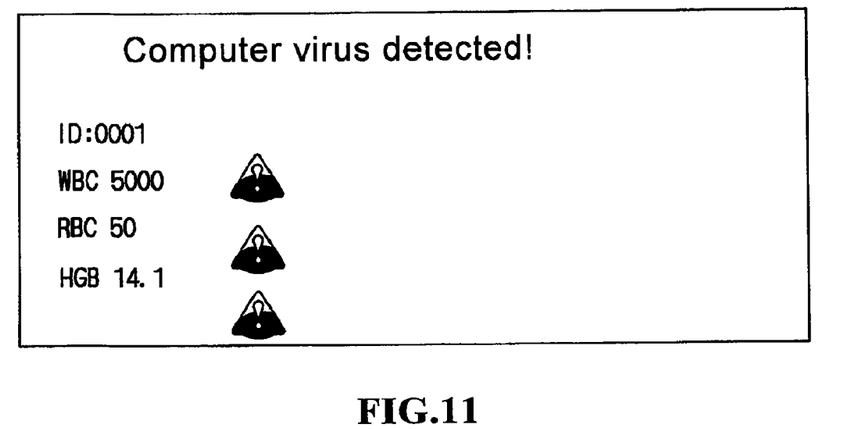
FIG. 11 shows an example of an analysis result display screen with warning information appended which is displayed on the display unit of the control device.

FIG. 11 shows an example of an analysis result display screen with warning information appended which is displayed on the display unit 140 of the control device 9. FIG. 11 is the screen displayed in step S1003 of FIG. 10, and shows a message indicating a malicious program (computer virus) has been detected, and a warning symbol appended to the analysis results after malicious program detection relative to the numeric values of the analysis results displayed for each sample ID identifying a sample.

Figure 12:
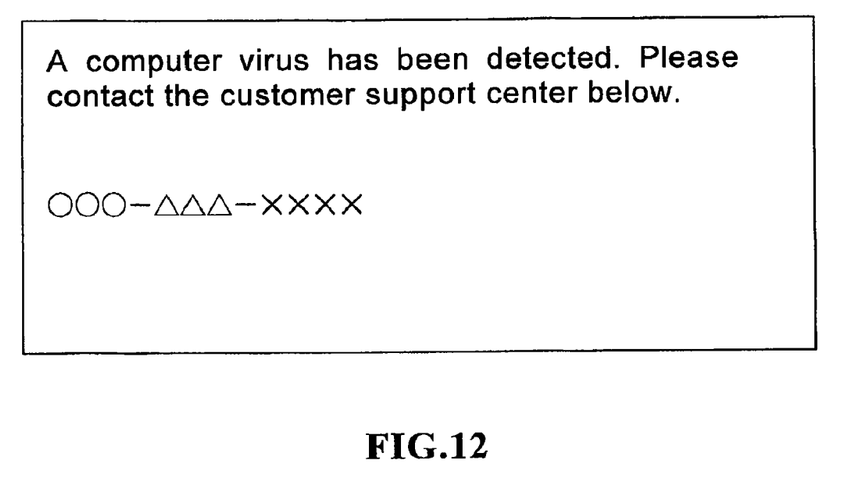
FIG. 12 shows an example of a warning information display screen which is displayed on the image display of the transport control device and the display unit of the control device.

FIG. 12 shows an example of a warning information display screen displayed on the image display 120 of the transport control device 8 or the display 140 of the control device 9. FIG. 12 is a screen displayed in steps S1006 and S1012 of FIG. 10; when a malicious program is redetected even after the malicious program deletion process has been executed, a massage is displayed urging custom support without continuing the process.

Note that when malicious program detection has been executed by a virus detection program, there is a possibility that analysis results are present which were already output after infection at the time of detection since it is unclear at what point the computer virus infection occurred. Accordingly, warning information may also be appended to the analysis results output prior to a predetermined period after the malicious program has been detected. The predetermined period is not specifically limited, and is preferably settable by the user to an optional period such as one hour, one day or the like. When the malicious program detection time is recorded with a time stamp, warning information may also be appended to the analysis results output before the time the previous malicious program was detected.

According to the above embodiment, when a malicious program such as a computer virus has been detected in the sample analyzer 1, the output can terminated for the analysis results of measurement data obtained after the malicious program was detected, or the user of the sample analyzer can prevent beforehand the reporting of the analysis results without verifying the low reliability by appending warning information to the analysis results.

Although the above embodiment discloses a sample analyzer 1 in which a plurality of transport devices 3 are connected to a plurality of measuring units 5, the transport device 3 may be connected to a single measuring unit 5, or no transport device need be provided at all. The control device 9 may be incorporated in the measuring unit 5 in a single integrated unit. The embodiment is not limited to a blood cell analyzer inasmuch as the embodiment is also applicable to immunoanalyzers, blood coagulation measuring apparatuses, biochemical analyzers, urine analyzers and the like.

Although the sample analyzer 1 is configured so as to be capable of connection to the network 10 in the above embodiment, recent years has seen increasing risk of infection by computer viruses via portable media such as a USB memory. Therefore, the sample analyzer 1 need not be configured so as to be capable of connection to a network.

Although the determination of the malicious program detection (steps S804 and S814) is started after a sample measurement start instruction has been received in the above embodiment, the determination of the malicious program detection may also start before the sample measurement start instruction has been received.

The present invention is not limited to the above embodiment and may be variously modified and rearranged insofar as such modifications are within the scope of the invention. For example, a plurality of transport control devices 8 and control devices 9 may be provided, and the network structure is not specifically limited. Alternatively, a single control computer provided with the functions of the transport control device 8 and control device 9 may be used.

What is claimed is:

1. A sample analyzer comprising:
    a measuring unit comprising: a measuring sample preparing section for preparing a measurement sample by mixing a medical sample obtained from a living body and a reagent; and a detector for detecting information reflecting a property of contents in the measurement sample and outputting a medical measurement data; and
    a measurement controller comprising a processor and a memory storing a computer program that enables the processor to carry out operations comprising:
    obtaining analysis results of the medical measurement data output from the measuring unit;
    detecting a malicious program in the memory storing the computer program for obtaining the analysis results of the medical measurement data; and
    restricting output of the obtained analysis results when a malicious program has been detected in the memory storing the computer program for obtaining the analysis results of the medical measurement data.

2. The sample analyzer of claim 1, wherein the restricting comprises outputting, together with the obtained analysis results, warning information indicating that a malicious program has been detected.

3. The sample analyzer of claim 1, further comprising:
    a transport device for transporting a sample to the measuring unit; and
    a transport controller configured for carrying out operations comprising:
    detecting a malicious program; and
    stopping the transport of the sample by the transport device when a malicious program has been detected.

4. The sample analyzer of claim 3, wherein the operations carried out by the transport controller further comprise:
    redetecting the malicious program when the sample transport has been stopped; and
    restarting the sample transport by the transport device when the malicious program is not detected by redetection.

5. The sample analyzer of claim 3,
    wherein the transport controller is connected to a network; and
    wherein the operations carried out by the transport controller further comprise disconnecting the transport controller from the network when a malicious program has been detected.

6. The sample analyzer of claim 5, wherein the operations carried out by the transport controller further comprise:
    redetecting the malicious program with the transport controller disconnected from the network; and
    reconnecting the transport controller to the network when the malicious program is not detected by redetection.

7. The sample analyzer of claim 6, further comprising:
    an identification reader for reading an identification attached to a sample container transported by the transport device; and
    wherein the operations carried out by the transport controller further comprise: transporting the sample to the identification reader after the transport device has been reconnected to the network.

8. The sample analyzer of claim 1,
wherein the operation carried out by the measurement controller further comprise: receiving a sample measurement start instruction of the measuring unit; and
wherein the measurement controller rejects the reception of the measurement start instruction when a malicious program has already been detected and a measurement start instruction has been received.

9. The sample analyzer of claim 1,
wherein the measurement controller is connected to a network; and
wherein the operations carried out by the measurement controller further comprise: disconnecting the measurement controller from the network when a malicious program has been detected.

10. The sample analyzer of claim 9, wherein the operations carried out by the measurement controller further comprise:
redetecting the malicious program with the measurement controller disconnected from the network; and
reconnecting the measurement controller to the network when the malicious program is not detected by redetection.

11. The sample analyzer of claim 1, wherein the operations carried out by the transport controller further comprise: outputting contact information to remove the malicious program when the malicious program has been detected.

12. The sample analyzer of claim 1, wherein the detection of the malicious program is executed continuously.

13. The sample analyzer of claim 2, further comprising: a display for displaying a screen comprising analysis results and warning information.

14. The sample analyzer of claim 1, wherein
the medical sample is a blood sample; and
the detector detects and outputs information reflecting a property of blood cells in the measurement sample, as the measurement data.

15. A sample analyzer comprising:
a measuring unit for preparing a measurement sample by mixing a medical sample obtained from a living body and a reagent; and for detecting information reflecting a property of contents in the measurement sample and outputting a medical measurement data; and
a measurement controller comprising a processor and a memory storing a computer program that enables the processor to carry out operations comprising:
obtaining analysis results of the medical measurement data output from the measuring unit;
detecting a malicious program in the memory storing the computer program for obtaining the analysis results of the medical measurement data; and when a malicious program has been detected in the memory storing the computer program for obtaining the analysis results of the medical measurement data, stopping measuring a sample by the measuring unit, obtaining analysis results of the measurement data, or outputting the analysis result.

16. A sample analyzing method performed by a computer which comprises a processor and a memory storing a computer program, the method comprising:
measuring a sample wherein measuring the sample comprises preparing a measurement sample by mixing a medical sample obtained from a living body and a reagent; and detecting information reflecting a property of contents in the measurement sample and outputting a medical measurement data; obtaining analysis results of the medical measurement data output from the medical sample;
detecting a malicious program in the memory storing the computer program for obtaining the analysis results of the medical measurement data; and
restricting output of the obtained analysis results when a malicious program has been detected in the memory storing the computer program for obtaining the analysis results of the medical measurement data.

17. The sample analyzing method of claim 16, wherein the restricting comprises outputting, together with the obtained analysis results, warning information indicating that a malicious program has been detected.

18. The sample analyzing method of claim 17, wherein
a measuring unit measures the sample, a controller obtains the analysis results and detects the malicious program, and a display displays the analysis results and the warning information.

19. The sample analyzing method of claim 16, wherein
the malicious program detection is executed continuously.

20. A non-transitory storage medium which stores computer-executable programs executed by at least one processor of a sample analyzer, comprising:
A non-transitory computer readable medium; and instructions, on the non-transitory computer readable medium, adapted to enable a general purpose computer to perform operations, comprising:
measuring a medical sample wherein measuring the medical sample comprises preparing a measurement sample by mixing a medical sample obtained from a living body and a reagent; and detecting information reflecting a property of contents in the measurement sample and outputting a medical measurement data;
obtaining analysis results of the medical measurement data output from the medical sample;
detecting a malicious program in the a memory storing the computer-executable program for obtaining the analysis results of medical measurement data; and
restricting the output of the obtained analysis results when a malicious program has been detected in the memory storing the computer-executable program for obtaining the analysis results of the medical measurement data.

* * * * *